(12) United States Patent
Larsen et al.

(10) Patent No.: US 10,078,021 B2
(45) Date of Patent: Sep. 18, 2018

(54) BODY CORE TEMPERATURE MEASUREMENT

(71) Applicant: Honeywell International Inc., Morris Plains, NJ (US)

(72) Inventors: Christopher Scott Larsen, Plymouth, MN (US); Brian Keith Olmsted, Richfield, MN (US)

(73) Assignee: Honeywell International Inc., Morris Plains, NJ (US)

( * ) Notice: Subject to any disclaimer, the term of this patent is extended or adjusted under 35 U.S.C. 154(b) by 372 days.

(21) Appl. No.: 14/862,671

(22) Filed: Sep. 23, 2015

(65) Prior Publication Data

US 2017/0079532 A1    Mar. 23, 2017

(51) Int. Cl.
| | |
|---|---|
| *G01K 13/00* | (2006.01) |
| *G01J 5/08* | (2006.01) |
| *A61B 5/01* | (2006.01) |
| *A61B 5/00* | (2006.01) |
| *G01J 5/12* | (2006.01) |
| *G01J 5/00* | (2006.01) |

(52) U.S. Cl.
CPC .............. *G01K 13/004* (2013.01); *A61B 5/01* (2013.01); *A61B 5/6817* (2013.01); *G01J 5/0011* (2013.01); *G01J 5/0806* (2013.01); *G01J 5/0818* (2013.01); *G01J 5/12* (2013.01); *A61B 2562/0233* (2013.01); *A61B 2562/0271* (2013.01)

(58) Field of Classification Search
CPC ................ G01K 13/002–13/004; G01J 5/0011
See application file for complete search history.

(56) References Cited

U.S. PATENT DOCUMENTS

| | | | | |
|---|---|---|---|---|
| 5,150,969 A | * | 9/1992 | Goldberg | .................. G01J 5/02 374/128 |
| 6,149,298 A | * | 11/2000 | Kraus | ........................ G01J 5/04 374/121 |
| 6,425,688 B1 | | 7/2002 | Hsu | |
| 6,522,912 B1 | | 2/2003 | Nakatani et al. | |
| 6,572,264 B1 | * | 6/2003 | Egawa | .................. G01J 5/0003 374/126 |
| 6,631,287 B2 | * | 10/2003 | Newman | .................... G01J 5/02 374/124 |

(Continued)

FOREIGN PATENT DOCUMENTS

| | | |
|---|---|---|
| CN | 106539567 | 3/2017 |
| JP | 2000-152916 A | 6/2000 |
| WO | WO-2006112837 A1 | 10/2006 |

*Primary Examiner* — Clayton E Labelle
*Assistant Examiner* — Leon W Rhodes, Jr.
(74) *Attorney, Agent, or Firm* — Schwegman Lundberg & Woessner, P.A.

(57) ABSTRACT

An apparatus for measuring body core temperature includes a light guide. The light guide can be coupled to an earpiece, or it can be a standalone device. The apparatus also includes a sensor positioned at one end of the light guide, and a processor coupled to the sensor. The sensor is operable to sense infrared radiation from an infrared source at the opposite end of the light guide. The processor is operable to determine a temperature of the infrared source at the opposite end of the light guide via a transfer function that correlates a measurement of the infrared radiation observed by the sensor and an effect of radiation of the light guide.

18 Claims, 4 Drawing Sheets

(56) References Cited

U.S. PATENT DOCUMENTS

| | | | |
|---|---|---|---|
| 7,036,978 B2 * | 5/2006 | Tabata | G01J 5/02 374/121 |
| 2009/0207882 A1 * | 8/2009 | Yu | G01J 5/0003 374/178 |
| 2013/0218022 A1 * | 8/2013 | Larsen | A61B 5/01 600/474 |

* cited by examiner

BODY CORE TEMPERATURE MEASUREMENT

GOVERNMENT FUNDING

This invention was made with Government support under contract number W911NF-14-C-0044 awarded by the U.S. Army and the Defense Advanced Research Projects Agency (DARPA). The United States Government has certain rights in this invention.

TECHNICAL FIELD

The present disclosure relates to body core temperature measurement.

BACKGROUND

Continuous or spot measurements of body core temperature through tympanic membrane (eardrum) thermometry generally require unrestricted access to the ear canal so that the temperature sensor's field of view can be completely filled by the tympanic membrane. In cases where the ear canal is obstructed by other components, or the subject presents different physiology, it can be very challenging for the temperature sensor itself (e.g., a thermopile) to reach all the way to the eardrum. As the standoff distance from the eardrum increases, the percentage of the region of interest diminishes as the square of the standoff distance, thereby rapidly increasing the difficulty in obtaining a reliable reading with a high degree of confidence. There is therefore a need for an optical design that allows the sensor to be located less deeply into the ear canal or even outside the ear canal, and yet still allows for the sensor's field of view to be substantially filled by the tympanic membrane.

DETAILED DESCRIPTION

Figure 1:
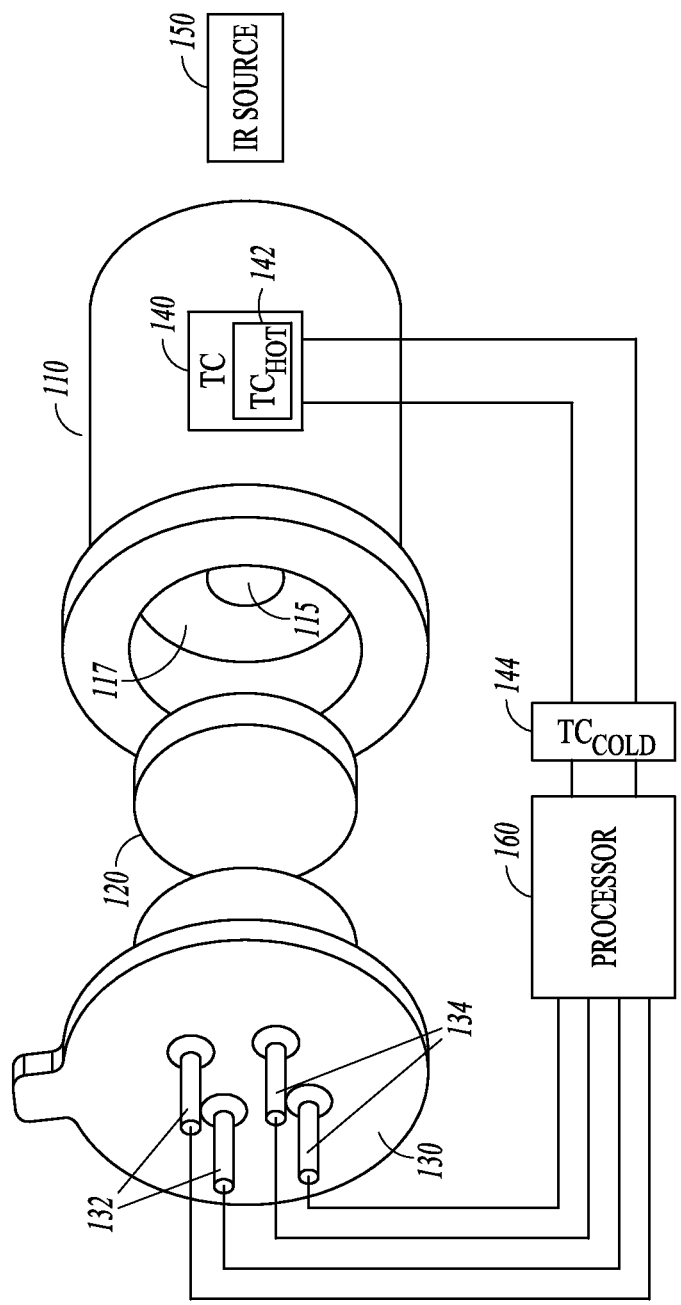
FIG. 1 illustrates an embodiment of a system and apparatus that is placed into an ear and that determines a body core temperature.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, electrical, and optical changes may be made without departing from the scope of the present invention. The following description of example embodiments is, therefore, not to be taken in a limited sense, and the scope of the present invention is defined by the appended claims.

As noted above, there is a need for continuous body core temperature monitoring. In an embodiment, this need is addressed with a device that can be coupled to an earpiece in the ear canal. The device can also be a standalone independent device. Whether a standalone device or coupled to an existing earpiece, the device is configured to be placed in an ear and retained in the ear. When used in conjunction with an existing earpiece (such as a communication device), the existing earpiece may have a hollow tube for sound conduction of audio in and out of the ear. However, the hollow tube of the existing earpiece and an associated sound sealing earplug leave little room for a thermopile sensor to go all the way in the ear canal to reach the tympanic membrane. Therefore, in an embodiment, an optical system is used that consists of a light guide and an optional lens. The light guide may be a hollow reflective tube, an optic fiber, or any other substance through which light and/or infrared radiation may propagate. When implemented with an existing earpiece, the light guide can be positioned next to and parallel to the hollow sound tube within the earpiece. The light guide is highly reflective to the long wave infrared (LWIR) radiation from the tympanic membrane, and guides the LWIR to the thermopile sensor (or other detector). In an embodiment, the light guide is much narrower in diameter than the thermopile itself, allowing use of a large, standard size (e.g., 4.6 mm diameter) thermopile with higher sensitivity, while still fitting in the ear canal alongside the other components (sound tubes, earplugs, etc.).

The light waveguide can be a rigid or a flexible tube with an LWIR reflective interior, for example, a reflective coating. In an embodiment, the waveguide's reduction in diameter from the thermopile diameter to the final exit diameter of the waveguide presents a flat surface to the thermopile sensor (i.e., a step change in diameter, as contrasted with a non-step change diameter that would be associated with a waveguide whose end was flared or tapered out at the thermopile sensor). In this way, the surface area of the waveguide viewed by the sensor is minimized, and the thermopile views the following objects—the flat surface of the waveguide where the diameter is reduced from the thermopile diameter to the waveguide tube diameter, a small spot of the eardrum as viewed via an optical ray straight through the waveguide, and the waveguide walls, which present a mix of reflections of the eardrum and the thermal radiation of the waveguide walls.

In cases wherein the waveguide's emissivity is constant, the eardrum temperature can be determined by measuring the thermopile observed temperature and then subtracting the effect of the waveguide temperature. If the waveguide is thermally conductive and it is closely and mechanically coupled to the thermopile or a can of the thermopile, the thermistor used in the thermopile package to measure the cold junction temperature of the thermopile should closely match the waveguide temperature. In this way, the system removes the effect of the waveguide optical radiation from the thermopile observed temperature, leaving only the eardrum temperature. The waveguide optical radiation can be determined empirically (e.g., via a regression analysis) to determine the transfer function between eardrum temperature and observed thermopile temperature. As noted above, an optional LWIR lens can be added between the thermopile and waveguide to reduce the percentage of the thermopile's field of view that is filled by the waveguide. This can reduce and possibly even eliminate the need to remove the waveguide's thermal radiation from the thermopile observed measurement.

In an embodiment, the thermal gradient along the light waveguide may cause inaccuracy in the body core temperature prediction. The thermal gradient arises from temperature differences between the tip of the waveguide, which is heated by the ear canal tympanic membrane), and the sensor end of the waveguide, which is heated by the ambient environment. An assumption that the ambient temperature is unchanging works well as an approximation when the regression coefficients for the thermopile (IR radiation-induced thermopile hot junction temperature from the eardrum) and the thermistor (cold junction temperature of the thermopile sensor) are chosen based on that one constant ambient temperature. However, when the ambient temperature changes, the waveguide temperature gradient changes, which affects the thermal emission magnitude from the waveguide. This means the regression coefficients are no longer valid, and the accuracy of the body core temperature function will be affected. The standard deviation of the computed target temperature error as viewed through the waveguide could possibly go from approximately 2 degrees C. of error at 25 degrees C. to nearly 4 degrees C. of error. This error magnitude is enough to make the predicted body core temperature less valuable with ambient temperatures that are any more than a few degrees different from the ambient temperature at which the regression coefficients were calibrated.

To address this effect from changes in ambient temperature, one can directly (or indirectly) measure the temperature at the light waveguide tip inside the ear canal (using another standoff temperature sensor or a contact sensor such as a thermocouple, thermopile, or a resistance temperature detector (RTD)), and the thermal gradient of the waveguide can be compensated for in the regression coefficients across the range of ambient temperature. Regression coefficients are computed by collecting thermopile hot and cold junction temperatures and waveguide tip temperatures across a known range of target, ambient, and waveguide tip temperatures, and then regression coefficients are computed for each of the measured temperatures. By applying this method, the standard deviation of temperature prediction error across the ambient temperature range of 25 C to 40 C could be improved from nearly 4 degrees C. to less than 1 degree C. This method accounts for differences in ambient temperature and differences in waveguide tip temperature. The waveguide tip temperature can be important when the device is first inserted into the ear, because the tip temperature will first be at room temperature (which is not the same as the eardrum body core temperature), and will slowly warm to ear canal skin temperature.

In different embodiments, the regression analysis can be a linear regression analysis or a regression analysis of higher order. As is known to those of skill in the art, linear regression is a subset of regression analysis that only allows linear terms. In such a regression analysis, there is a truth data point such as a body temperature measurement taken by a reliable instrument. There are also four other temperature measurements. Specifically, a thermopile (or other sensor at the end of the light waveguide that is distant from the tympanic membrane) cold junction temperature, a thermopile hot junction temperature, a thermocouple (or other sensor at the end of the light waveguide that is proximate to the tympanic membrane) cold junction temperature, and a thermocouple hot junction temperature. The true body temperature is treated as a dependent variable that depends on the other four measurements. Data are collected for all five temperature values (i.e., the body temperature, thermopile hot junction temperature, thermopile cold junction temperature, thermocouple hot junction temperature, and thermocouple cold junction temperature), and the collected data as matched data sets are put into a regression analysis program, such as a Matlab regression analysis. The regression analysis generates coefficients $\alpha$, $\beta$, $\gamma$, and $\delta$ that best match the data for the following function:

$$\text{Body temperature}=\alpha(TP_{Hot})+\beta(TP_{Cold})+\gamma(TC_{Hot})+\delta(TC_{Cold}) \quad \text{Equation No. 1}$$

wherein TP represents a thermopile and TC represents a thermocouple. The regression analysis also generates a magnitude of the error for the collected data. This regression analysis is performed over many different systems, which illustrates that the same coefficients can be used for every system, every person, and every condition. After showing that the same coefficients can be used for each system, the coefficients are loaded in every unit and the units then can provide accurate body temperature measurements in all situations. In an alternative embodiment, a user of the system could input their true body temperature when the earpiece is placed into their ear, and the regression calibration could be done for that particular user. In another alternative embodiment, the light waveguide could be pointed at something with a known temperature before each use, and the regression calibration could be calculated using that known temperature.

The light waveguide can be created from low emissivity material to maximize the ratio of internally reflected light to emitted light from the waveguide itself. The waveguide may have high thermal conductivity to minimize the thermal gradient present between the tip (i.e. proximate the tympanic membrane) and the sensor (i.e., distal from the tympanic membrane). The waveguide geometry may be chosen to accommodate a wide range of ear canal physiology. As noted above, the waveguide may have a cup or can that fully encompasses the thermopile sensor to restrict its field of view to light that is either emitted by the waveguide or emitted into the tip of the waveguide from the tympanic membrane. The waveguide may be made from machined or bent aluminum or copper. Copper is easy to coat with gold, which is a low emissivity material that will not oxidize. When the waveguide is a hollow copper tube, the interior of the copper tube can be coated with gold. The gold coating also generally helps with oxidative resistance. The waveguide could also be an optic fiber. The waveguide tip temperature may be measured by a thermocouple, an RTD, or a thermistor. The thermopile and waveguide tip temperature sensors may both be routed to the same analog to digital converter to digitize the measurements, and the digitized measurements may then be fed into an equation (such as Equation No. 1) with the calibrated regression coefficients to determine the target (eardrum) temperature.

Figure 2:
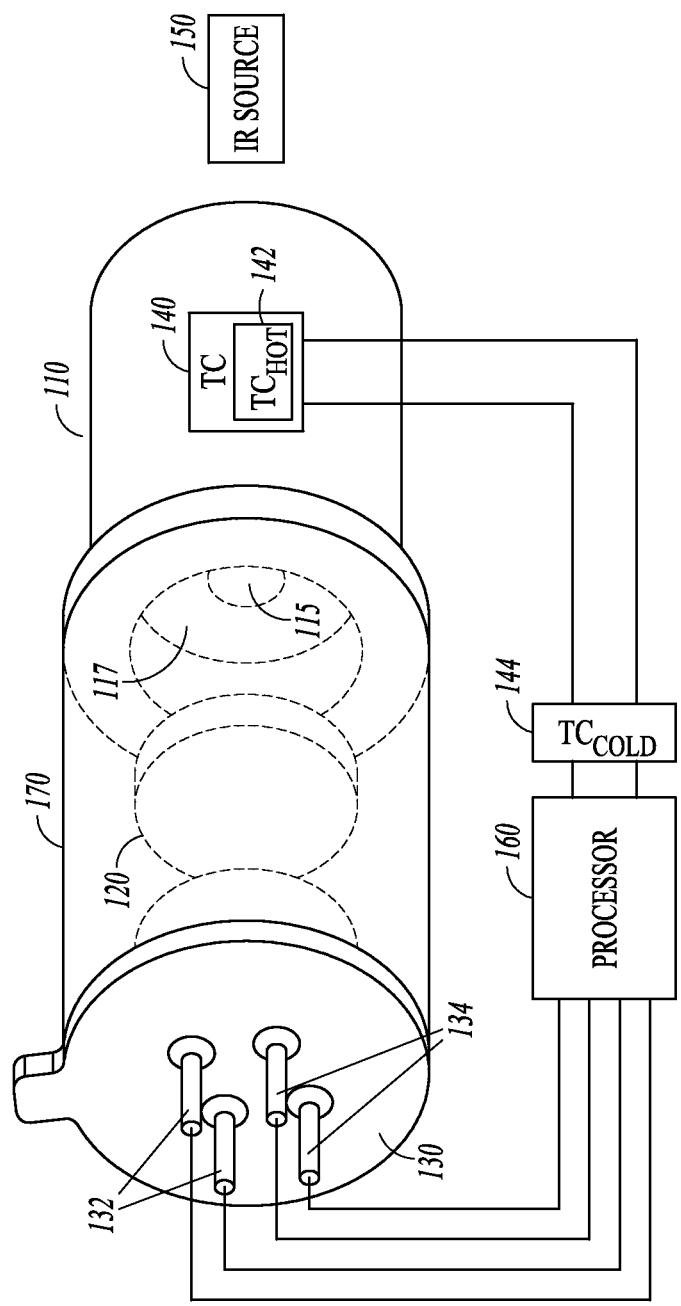
FIG. 2 illustrates another embodiment of a system and apparatus that is placed into an ear and that determines a body core temperature.

FIG. 1 is a block diagram illustrating an embodiment of a system and apparatus that is placed into an ear and that determines a body core temperature. The system includes a light waveguide 110, an optional lens 120, a thermopile (or other temperature sensing device) 130, and a thermocouple (or other temperature sensing device) 140. The waveguide 110 in an embodiment can be about 20 mm long and about 2 mm in diameter, and includes a waveguide hole 115 that traverses the length of the waveguide. The apparatus, and in particular the thermopile 130 and thermocouple 140, is coupled to a processor 160. Specifically, the hot junction 132 and cold junction 134 of the thermopile, and the hot junction 142 and the cold junction 144 of the thermocouple are coupled to the processor 160. The apparatus is placed next to an IR source 150, such as a tympanic membrane. As noted above, a true temperature of the IR source is obtained, and the system is calibrated over a temperature gradient using the hot and cold junctions 132, 134, 142, and 144 of the thermopile 130 and thermocouple 140. In an embodiment, the apparatus further includes a lens 120, which reduces the field of view of the sensor that is occupied by the light waveguide. The end of the waveguide can also include a can, container, or protective housing 170 as illustrated in FIG. 2 that, in conjunction with the waveguide's reduction in diameter from the thermopile diameter to the final exit diameter of the waveguide presenting the flat surface 117 to the thermopile sensor (i.e., a step change in diameter), further limits the infrared radiation from the ambient environment that is sensed by the thermopile.

Figure 3:
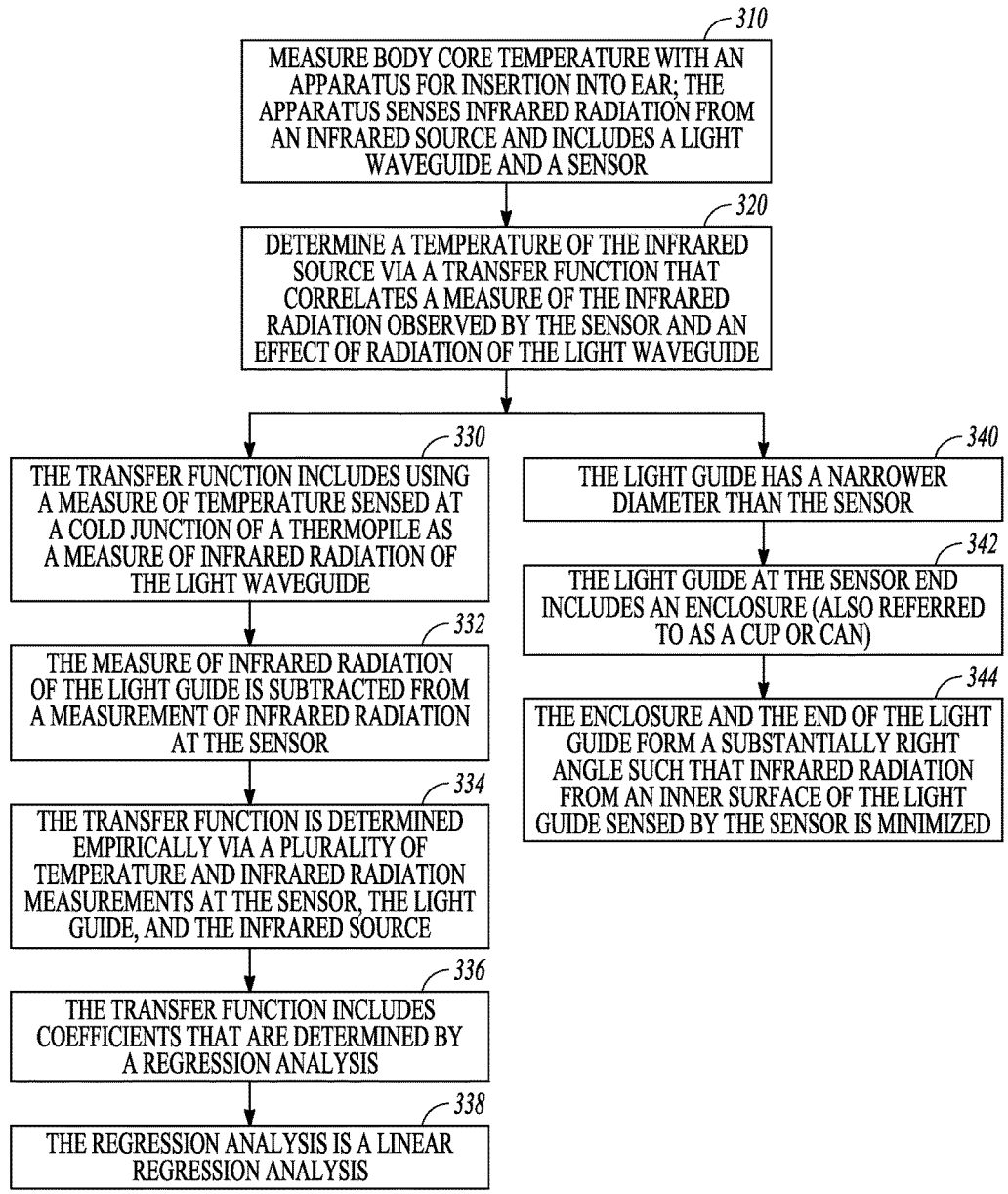
FIG. 3 is a block diagram illustrating features and operations of a system and apparatus that is placed into an ear and that determines a body core temperature.
Figure 4:
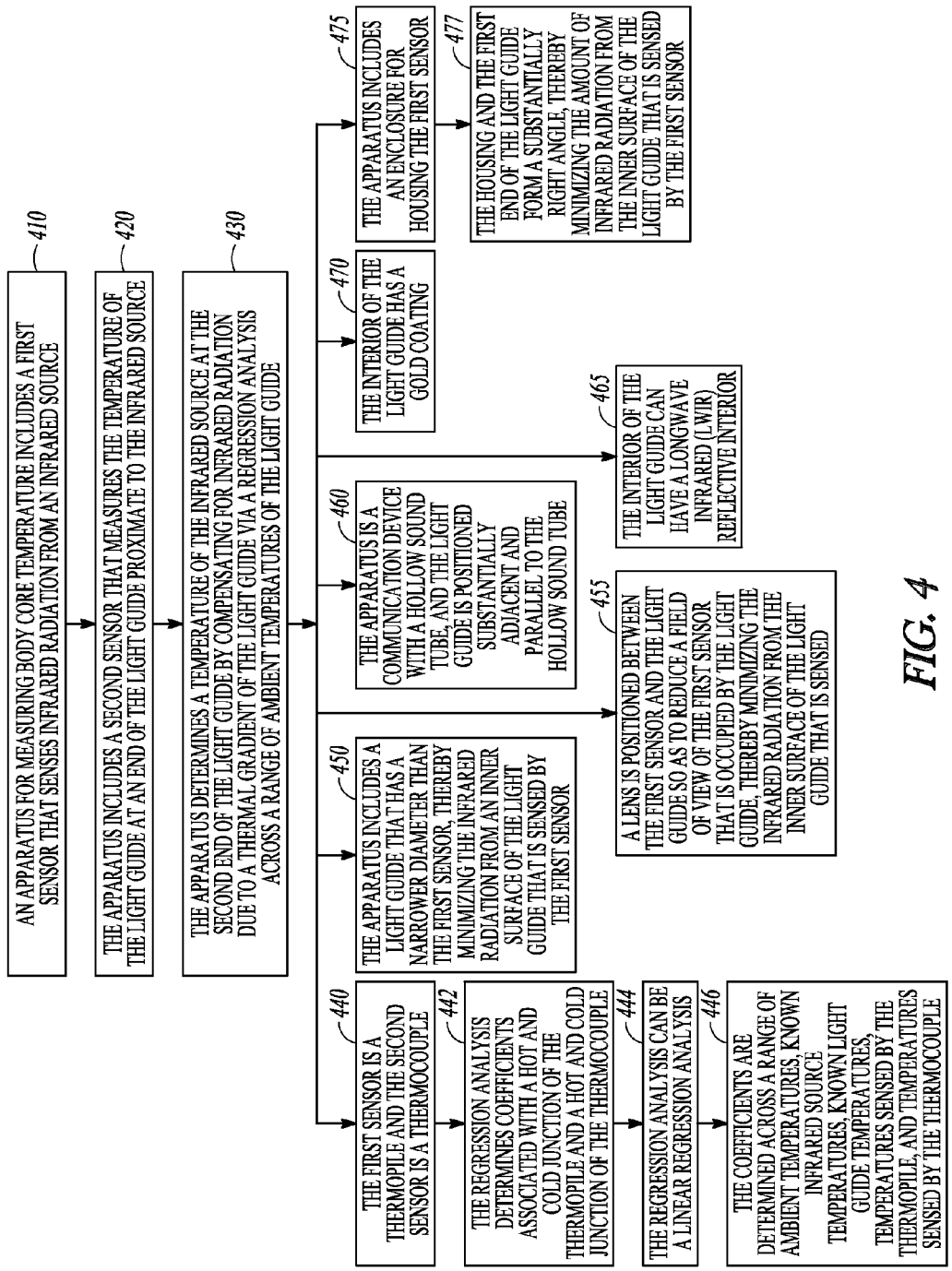
FIG. 4 is a block diagram illustrating features and operations of another system and apparatus that is placed into an ear and that determines a body core temperature.

FIGS. 3 and 4 are block diagrams illustrating features and operations of systems and apparatuses that are placed into an ear and that determines a body core temperature. FIGS. 3 and 4 include a number of process blocks 310-344 and 410-477 respectively. Though arranged substantially serially in the examples of FIGS. 3 and 4, other examples may reorder the blocks, omit one or more blocks, and/or execute two or more blocks in parallel using multiple processors or a single processor organized as two or more virtual machines or sub-processors. Moreover, still other examples can implement the blocks as one or more specific interconnected hardware or integrated circuit modules with related control and data signals communicated between and through the modules. Thus, any process flow is applicable to software, firmware, hardware, and hybrid implementations.

Referring to FIG. 3, at 310, an apparatus for measuring body core temperature senses infrared radiation from an infrared source. In an embodiment, the apparatuses of FIGS. 1 and/or 2 can be used to sense the infrared radiation. Specifically, the light guide of the apparatus, which can be a hollow tube and which can include an internally reflective surface, senses the infrared radiation from the infrared source (such as a tympanic membrane) at the one end of the light guide, the infrared radiation is propagated via the light guide to the other end of the light guide, and a sensor positioned at the other end of the light guide senses the infrared radiation. At 320, a processor coupled to the sensor at the other end of the light guide determines a temperature of the infrared source at the one end of the light guide via a transfer function that correlates a measurement of the infrared radiation observed by the sensor and an effect of radiation of the light guide.

As indicated at 330, the transfer function includes using a measure of temperature sensed at a cold junction of a thermopile as a measure of infrared radiation of the light guide. At 332, the measure of infrared radiation of the light guide is subtracted from a measurement of infrared radiation at the sensor. As is known to one of skill in the art, a cold temperature of a thermopile is a contact measurement and therefore measures temperature. As is also known to those of skill in the art, a hot junction of the thermopile can explicitly measure infrared radiation. The light guide and the temperature sensor should have good mechanical coupling, and therefore should be at the same temperature. At 334, the transfer function is determined empirically via a plurality of temperature and infrared radiation measurements at the sensor, the light guide, and the infrared source. It is worth noting here that not all of the measurements will be of infrared radiation. As indicated at 334, some measurements will be of temperature. Specifically, in an embodiment, the light guide is a direct contact temperature measurement that allows compensation for the infrared radiation of the light guide that is picked up by the sensor via the hot junction of the thermopile. At 336, and as explained above, the transfer function includes coefficients that are determined by a regression analysis. At 338, the regression analysis is a linear regression analysis.

In an embodiment, the light guide has a narrower diameter than the sensor (340). At 342, the light guide at the sensor end includes an enclosure (also referred to as a cup or can). The cup or can receives or encloses the sensor, and as indicated at 344, the enclosure and the end of the light guide form a substantially right angle such that infrared radiation from an inner surface of the light guide sensed by the sensor is minimized. This minimization of the infrared radiation from the inner surface of the light guide of course results in the vast majority of the infrared radiation that is sensed by the sensor originating from the infrared source (e.g., tympanic membrane) and not the inner surface of the light guide.

Referring to FIG. 4, at 410, an apparatus for measuring body core temperature includes a first sensor that senses infrared radiation from an infrared source. The apparatus includes a light guide with a first and second end, and which is made up of an internally reflective tube (in another embodiment, the light guide is an optic fiber). The light guide is coupled to an earpiece. The first sensor of the apparatus senses the infrared radiation at the second end of the light guide (via the transmission of the infrared radiation through the light guide). In addition to the first sensor, which is positioned at the first end of the light guide distal from the infrared source, the apparatus includes a second sensor that is positioned at the second end of the light guide proximate to the infrared source. The apparatus also includes a computer processor that is coupled to the first sensor and the second sensor.

At 420, the second sensor measures the temperature of the light guide at the second end of the light guide proximate to the infrared source. At 430, the processor determines a temperature of the infrared source at the second end of the light guide by compensating for infrared radiation due to a thermal gradient of the light guide via a regression analysis across a range of ambient temperatures of the light guide.

In an embodiment, as indicated at 440, the first sensor can be a thermopile and the second sensor can be a thermocouple. At 442, the regression analysis determines coefficients associated with a hot and cold junction of the thermopile and a hot and cold junction of the thermocouple. As indicated at 444, the regression analysis can be a linear regression analysis. At 446, the coefficients are determined across a range of ambient temperatures, known infrared source temperatures, known light guide temperatures, temperatures sensed by the thermopile, and temperatures sensed by the thermocouple.

FIG. 4 further indicates that the body core temperature measuring apparatus can include many of the features of the apparatus of FIG. 3. For example, the apparatus of FIG. 4 can also include a light guide that has a narrower diameter than the first sensor. As discussed above, this feature minimizes the infrared radiation from an inner surface of the light guide that is sensed by the first sensor (450). In another embodiment, as illustrated at 455, a lens is positioned between the first sensor and the light guide so as to reduce a field of view of the first sensor that is occupied by the light guide. This feature, like the narrower diameter of the light guide discussed at 450, minimizes the infrared radiation from the inner surface of the light guide that is sensed.

As indicated at 460, the earpiece apparatus is a communication device with a hollow sound tube, and the light guide is positioned substantially adjacent and parallel to the hollow sound tube. When the light guide is hollow, the interior of the light guide can have a longwave infrared (LWIR)

reflective interior (465), and in another embodiment the interior of the light guide has a gold coating (470).

Also like the apparatus of FIG. 3, the light guide of the apparatus of FIG. 4 can include an enclosure for housing the first sensor (475). As noted above, the housing and the first end of the light guide form a substantially right angle (477). This right angle minimizes the amount of infrared radiation from the inner surface of the light guide that is sensed by the first sensor (as compared to, for example, an end of a light guide that is tapered or flared out).

It should be understood that there exist implementations of other variations and modifications of the invention and its various aspects, as may be readily apparent, for example, to those of ordinary skill in the art, and that the invention is not limited by specific embodiments described herein. Features and embodiments described above may be combined with each other in different combinations. It is therefore contemplated to cover any and all modifications, variations, combinations or equivalents that fall within the scope of the present invention.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. An apparatus for measuring body core temperature comprising:
    a light guide comprising an internally reflective tube, the light guide coupled to an earpiece, the light guide having a first end and a second end;
    a sensor positioned at the first end of the light guide; and
    a processor coupled to the sensor;
    wherein the sensor is operable to sense infrared radiation from an infrared source at the second end of the light guide;
    wherein the processor is configured to determine a temperature of the infrared source at the second end of the light guide via a transfer function that correlates a measure of the infrared radiation observed by the sensor and an effect of radiation of the light guide;
    wherein the sensor comprises a thermopile; and
    wherein the transfer function comprises using a measurement of temperature sensed at a cold junction of the thermopile as a measurement of infrared radiation of the light guide, and subtracting the measurement of infrared radiation of the light guide from a measurement of infrared radiation at the sensor.

2. The apparatus of claim 1, wherein the transfer function is determined empirically via a plurality of temperature and infrared radiation measurements at the sensor, the light guide, and the infrared source.

3. The apparatus of claim 2, wherein the transfer function comprises coefficients determined by a regression analysis.

4. The apparatus of claim 3, wherein the regression analysis comprises a linear regression analysis.

5. The apparatus of claim 1, wherein the infrared source comprises an eardrum.

6. The apparatus of claim 1, wherein the light guide comprises a narrower diameter than the sensor.

7. The apparatus of claim 1, comprising a lens positioned between the sensor and the light guide so as to reduce a field of view of the sensor that is occupied by the light guide.

8. The apparatus of claim 1, wherein the earpiece comprises a communication device and a hollow sound tube, and wherein the light guide is positioned substantially adjacent and parallel to the hollow sound tube.

9. The apparatus of claim 1, wherein the light guide comprises a longwave infrared (LWIR) reflective interior.

10. The apparatus of claim 1, wherein the light guide comprises a hollow tube, and an interior of the light guide comprises a gold coating.

11. The apparatus of claim 1, wherein the first end of the light guide comprises an enclosure for receiving the sensor.

12. The apparatus of claim 11, wherein the enclosure and the first end of the light guide form a substantially right angle such that infrared radiation from an inner surface of the light guide sensed by the sensor is minimized.

13. The apparatus of claim 1, wherein the light guide comprises a length of about 20 millimeters and a diameter of about 2 millimeters.

14. The apparatus of claim 1, wherein the earpiece comprises a stand alone earpiece operable for placing and retaining in an ear.

15. An apparatus for measuring body core temperature comprising:
    a light guide having a first end and a second end;
    a sensor positioned at the first end of the light guide; and
    a processor coupled to the sensor;
    wherein the sensor is operable to sense infrared radiation from an infrared source at the second end of the light guide;
    wherein the processor is configured to determine a temperature of the infrared source at the second end of the light guide via a transfer function that correlates a measure of the infrared radiation observed by the sensor and an effect of radiation of the light guide;
    wherein the sensor comprises a thermopile; and
    wherein the transfer function comprises using a measurement of temperature sensed at a cold junction of the thermopile as a measurement of infrared radiation of the light guide, and subtracting the measurement of infrared radiation of the light guide from a measurement of infrared radiation at the sensor.

16. The apparatus of claim 15, wherein the light guide is coupled to an earpiece.

17. The apparatus of claim 15,
    wherein the transfer function is determined empirically via a plurality of temperature and infrared radiation measurements at the sensor, the light guide, and the infrared source; and
    wherein the transfer function comprises coefficients determined by a regression analysis.

18. The apparatus of claim 15, comprising a lens positioned between the sensor and the light guide so as to reduce a field of view of the sensor that is occupied by the light guide.

* * * * *